(12) United States Patent
Keller et al.

(10) Patent No.: US 7,921,703 B2
(45) Date of Patent: Apr. 12, 2011

(54) INTEGRATED OIL CONDITION AND LEVEL SENSOR

(75) Inventors: Robert Dean Keller, Davisburg, MI (US); Gerrit VanVranken Beneker, Lake Orion, MI (US)

(73) Assignee: Eaton Corporation, Cleveland, OH (US)

( * ) Notice: Subject to any disclaimer, the term of this patent is extended or adjusted under 35 U.S.C. 154(b) by 457 days.

(21) Appl. No.: 12/101,520

(22) Filed: Apr. 11, 2008

(65) Prior Publication Data

US 2008/0250851 A1 Oct. 16, 2008

Related U.S. Application Data

(60) Provisional application No. 60/922,922, filed on Apr. 11, 2007.

(51) Int. Cl.
*G01M 15/09* (2006.01)
(52) U.S. Cl. .................................. 73/114.55
(58) Field of Classification Search ............... 73/53.05, 73/54.23, 54.25, 54.26, 54.37, 114.55, 114.56; 340/450.3
See application file for complete search history.

(56) References Cited

U.S. PATENT DOCUMENTS

| 2,285,255 | A | * | 6/1942 | Davis ........................ 73/160 |
| 4,762,000 | A | | 8/1988 | Bond, Jr. |
| 2005/0212533 | A1 | | 9/2005 | Itomi |
| 2008/0093172 | A1 | | 4/2008 | Albertson |
| 2008/0250851 | A1 | | 10/2008 | Keller |
| 2010/0281971 | A1 | * | 11/2010 | Beneker et al. .......... 73/290 R |

FOREIGN PATENT DOCUMENTS

| DE | 4125588 A1 | 2/1993 |
| DE | 19902991 C1 | 7/2000 |
| DE | 10242959 A1 | 11/2003 |
| WO | 8603297 | 6/1986 |
| WO | 9113322 | 9/1991 |

* cited by examiner

*Primary Examiner* — John Fitzgerald
(74) *Attorney, Agent, or Firm* — Quinn Law Group, PLLC (57) ABSTRACT

An oil condition and level sensor is provided that includes a solenoid body, a coil, an armature and a pole piece. The solenoid body defines an armature chamber between the armature and the pole piece. The armature is movable in the armature chamber in response to energizing of the coil. In an oil condition sensing system, the coil is operatively connected to a controller which can determine at least one of an oil temperature, oil viscosity, oil level, and an oil change occurrence. In one embodiment, four oil levels, including an overfill oil level and an excessively low oil level may be detected. The sensor is referred to as an integrated oil condition and level sensor as multiple sensing functions are integrated into one sensor.

22 Claims, 5 Drawing Sheets

INTEGRATED OIL CONDITION AND LEVEL SENSOR

CROSS-REFERENCE TO RELATED APPLICATIONS

This application claims the benefit of U.S. Provisional Application 60/922,922, filed Apr. 11, 2007, which is hereby incorporated by reference in its entirety.

TECHNICAL FIELD

The present invention relates to oil sensors.

BACKGROUND OF THE INVENTION

Newer vehicles often have extended warranties that allow vehicle manufacturers to cover repairs for higher mileage vehicles. Regular oil changes are often a condition of maintaining warranty coverage. To ensure proper maintenance, an oil condition and level sensor may be incorporated into the vehicle to monitor the condition of the oil, alert the driver when an oil change is needed, and to detect whether an oil change has occurred.

In the past, oil change frequency was dictated by rules of thumb (e.g., every 3000 miles). However, newer technologies in oil additives and vehicle tuning can extend the time and distance between changes. Moreover, better understanding of the effects of the vehicle's operation on oil condition and improved engine controller computing power allows oil change frequency to be customized and predicted based on the oil's actual condition.

SUMMARY OF THE INVENTION

An oil condition and level sensor is provided that includes a solenoid body, a coil, an armature and a pole piece. The solenoid body defines an armature chamber between the armature and the pole piece. The armature is movable in the armature chamber in response to energizing of the coil. In an oil condition sensing system, the coil is operatively connected to a controller which can determine at least one of an oil temperature, oil viscosity, oil level, and an oil change occurrence. In one embodiment, four oil levels may be detected, including an overfill oil level and an excessively low oil level. The sensor is referred to as an integrated oil condition and level sensor as multiple sensing functions are integrated into one sensor. The sensor may be used in many different applications where there is a need to measure fluid level, fluid viscosity and/or fluid temperature, such as in engines, food processing, stationary press oil gear boxes, and fluid cooling systems.

The armature, the pole piece, and the solenoid body define multiple orifices and chambers configured to establish positive displacement of fluid through the armature chamber as the armature travels. Travel time of the armature in the armature chamber corresponds to the resistance to fluid flow through the orifices. The "fluid flow" through each respective orifice may be air, a liquid, such as oil, or a combination of both, and depends upon the oil level.

For example, the armature defines a first orifice in communication with the armature chamber. The pole piece defines a second orifice in communication with the armature chamber. The orifices are configured such that fluid enters and is displaced from the armature chamber through the orifices as the armature moves, and movement of the armature within the armature chamber is thereby affected by resistance to fluid flow through the orifices. A pressure differential is created within the armature chamber if the first and second orifices are different sizes, causing displacement of fluid into and out of the armature chamber through the orifices as the armature moves in a vertical direction. The sensor is configured to be immersed in oil within an oil pan at a full condition. The travel time of the armature within the armature chamber is related to the viscosity of fluid flowing through the chamber and orifices. For example, if oil level is low, air, rather than oil, will be drawn into the armature chamber. Because air flows much more freely than oil, the average armature travel time, also referred to as response time, will be shorter when oil is low. Thus, the "fluid flow" within the chamber and orifices discussed herein may be either air or oil.

The pole piece may have a substantially conical profile in order to slow movement of the armature within the armature chamber. By slowing movement of the armature, the gain of current drawn from the coil corresponding with travel time of the armature is increased. A conical profile of the pole piece eliminates acceleration of the armature as it moves, providing a nearly linear viscosity versus velocity curve, making the response time characteristic more consistent to more accurately detect the oil condition. Check valves, sealing mechanisms and biasing mechanisms may be used to further slow armature travel and create positive displacement within the various chambers.

The above features and advantages and other features and advantages of the present invention are readily apparent from the following detailed description of the best modes for carrying out the invention when taken in connection with the accompanying drawings.

DESCRIPTION OF THE PREFERRED EMBODIMENTS

Figure 1:
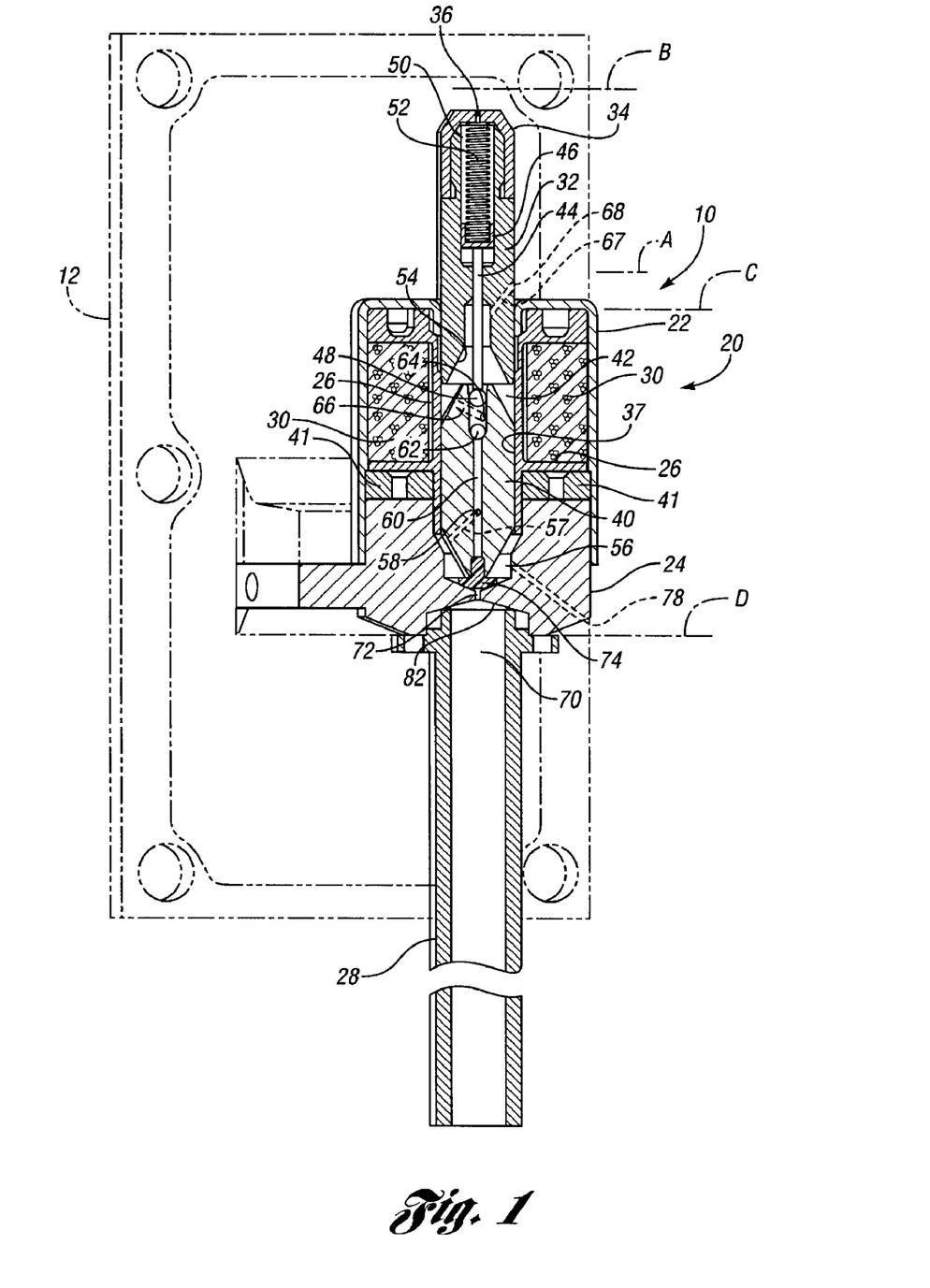
FIG. 1 is a schematic perspective cross-sectional illustration of a first embodiment of an oil condition and level sensor.
Figure 2:
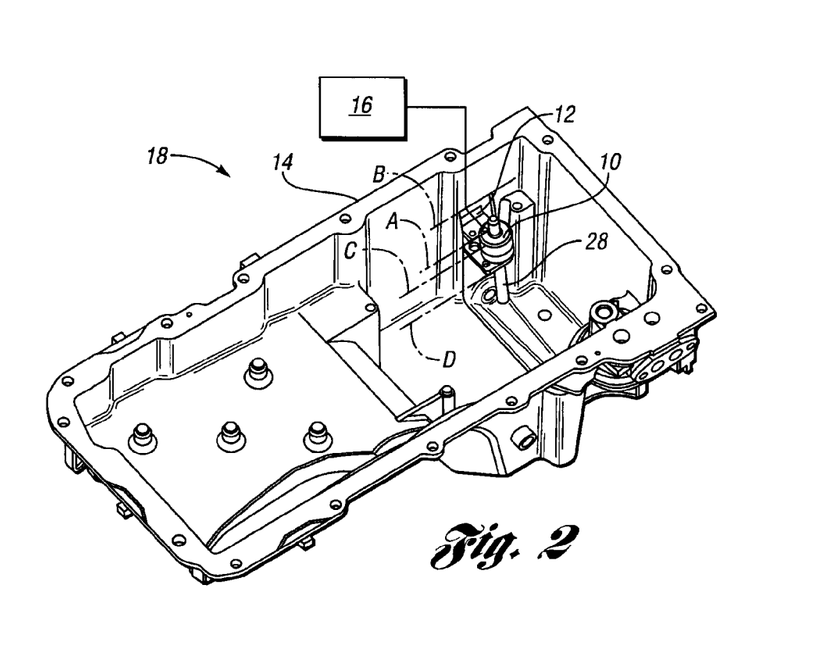
FIG. 2 is a schematic perspective illustration of an oil condition sensing system including the oil condition and level sensor of FIG. 1 mounted in an oil pan with a controller connected to the sensor.

Referring to the drawings, wherein like reference numbers refer to like components, FIG. 1 shows an oil condition and level sensor 10 supported on a mounting bracket 12. In FIG. 2, the mounting bracket 12 is secured to an oil pan 14, such as an engine oil pan on a vehicle, so that the oil condition and level sensor 12 is positioned in the oil pan 14 to enable detection of multiple oil conditions, including oil temperature, oil viscosity, an oil change occurrence, and multiple oil levels, as further described herein. The oil condition and level sensor 10 is operatively connected to an electronic controller 16, which may be contained either inside or outside of the oil pan, such as on a vehicle transmission or elsewhere in the vehicle, to establish an oil condition sensing system 18.

Referring to FIG. 1, the oil condition and level sensor 10 is shown in greater detail. A solenoid body 20 includes an outer portion 22, also referred to as a can, a base portion 24, a coil support portion 26, an extension portion 28 and a cap portion 34. The coil support portion 26 (also referred to as a bobbin) surrounds a coil 30. The outer portion 22, base portion 24, coil support portion 26, extension portion 28, and cap portion 34 may be made integral or made unitary with one another by casting, molding, or other processes.

A pole piece 32 is press-fit or otherwise secured within the outer portion 22. The cap portion 34 surrounds a distal end of the pole piece 32 and has an orifice 36 therethrough (the orifice 36 is referred to herein as a sixth orifice or as another orifice). The pole piece 32, outer portion 22, coil 30, flux collector 41 and armature 40 form an electromagnet. Lines of flux are created in an air gap between the pole piece 32 and the armature 40 when the coil 30 is energized by an electric source (such as a battery, not shown).

An armature 40 is movable within a columnar cavity 37 defined by the coil support portion 26 and the base portion 24, with the armature 40 partially defining an armature chamber 42 between the armature 40 and the pole piece 32 that varies in volume as the armature 40 moves in response to the flux created by energizing the coil. Flux collectors 41 are positioned adjacent the armature 40. The solenoid body 20, armature 40 and pole piece 32 have many features designed to slow travel time of the armature 40 to increase the gain of (i.e., the time until occurrence of) the signature inductive kick that indicates an end of travel. By slowing travel time and thereby increasing the gain, relative differences in travel time as a result of changes in oil viscosity, oil level or an oil change occurrence are magnified (i.e., the sensitivity of the sensor 10 is increased), and therefore the oil conditions are more accurately diagnosed and tracked by the controller 16.

Figure 6:
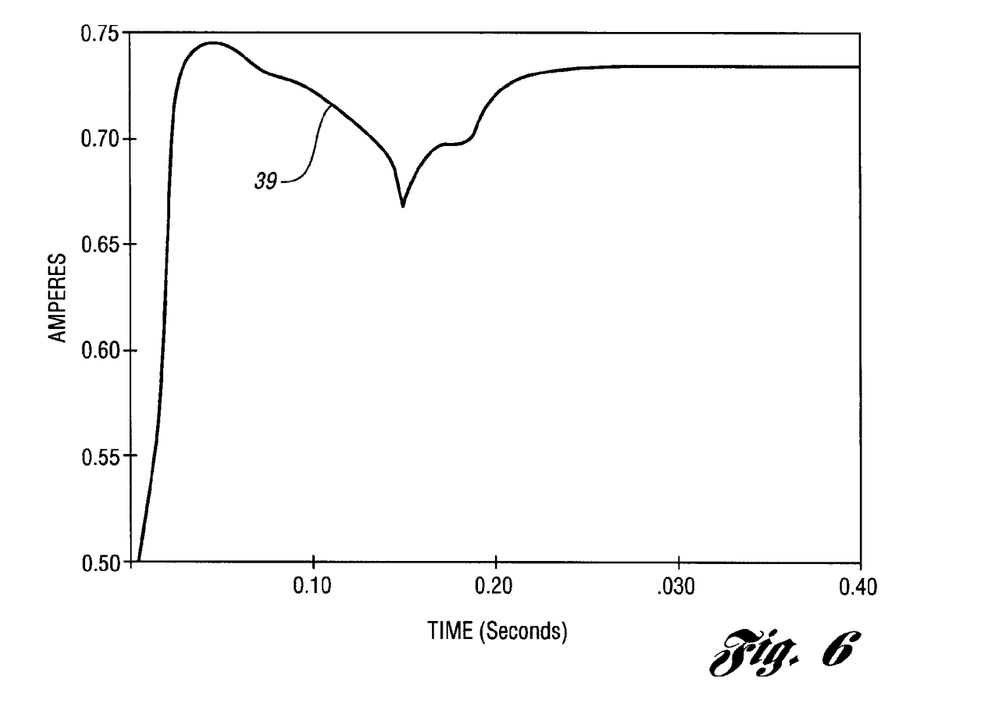
FIG. 6 is a schematic graph of an exemplary current draw versus time for a traveling armature in any of the oil condition and level sensors of FIGS. 1-5, illustrating inductive kick phenomena.

Referring to FIG. 6, an exemplary plot of current draw versus time results in a current draw curve 39 with an inductive kick illustrated as a distinct dip followed by an increase in current draw indicative of the solenoid armature 40 reaching an end of travel under known oil temperature (25 degrees Celsius) and oil fill level (oil level set at low, resulting in the relatively quick inductive kick at 0.15 seconds). The plot of FIG. 6 is exemplary only, and the level of current draw and time to inductive kick (i.e., armature travel time) may vary as described herein.

A rod 44 may be secured or not secured at one end to a piston 46. A plug-like element, referred to herein as a ball 48 is press-fit, welded or otherwise secured to the armature 40 at an opposing end. Although referred to as a ball 48, a non-spherical plug-like element may be used in lieu of the ball 48. The ball 48 does not move relative to the armature 40. When magnetic flux of the sensor 10 drives the armature 40, the piston 46 moves within a pole piece chamber 50 in the pole piece 32. A biasing mechanism, which in this case is a spring 52, biases the armature 40 away from the pole piece 32. The pole piece 32 has an inner surface with a conical profile 54 interfacing with a like conical profile of an outer surface of the armature 40. The conical profile 54 distributes flux over a larger air gap adjacent the armature 40 than would a flat pole piece profile, thus slowing armature travel time.

A second body chamber 56 is formed in the base portion 24. A first orifice 58 in the armature is in fluid communication with the second chamber 56 through channel 57 (shown in phantom) running through a different section of the armature 40. A channel 60 through the armature 40 is selectively opened and closed by a ball check valve 62. Another orifice 64 in the armature 40 (referred to herein as a fourth orifice) is between the fixed ball 48 and a movable ball or plug of the ball check valve 62. The orifice 64 is in fluid communication with the armature chamber 42 via a channel 66. Another orifice 68 in the pole piece 32 (referred to herein as a second orifice) is in fluid communication with the armature chamber 42 and with the surrounding oil pan 14.

When the armature 40 moves away from the pole piece 32, the movable ball of valve 62 moves away from the channel 60, allowing flow from the second body chamber 56 to the armature chamber 42 through the orifices 58 and 64 and channels 57, 60 and 66, thereby allowing the sensor 10 to act as a positive displacement pump, as opposed to passive pumping action which occurs without the closure of the ball check valve 62. Size differences between the orifices also contribute to positive displacement. When the armature 40 moves toward the pole piece 32, the movable ball covers the channel 60, forcing fluid in the armature chamber 42 out of the second orifice 68 via passage 67.

The extension portion 28 has a chamber 70 referred to herein as a first body chamber or a lower chamber, as it is positioned lower in the oil pan 14 than the remainder of the sensor 10, as is evident in FIG. 2. The base portion 24 has an orifice 72, referred to herein as a third orifice, that fluidly connects the second body chamber 56 with the first body chamber 70. The armature 40 has a sealing mechanism 74, which in this embodiment is an elastomeric seal, that seals the third orifice 72, preventing fluid flow from the first chamber 70 to the second chamber 56 when the armature 40 is biased by the spring 52 to the extreme lowered position of FIG. 1 (e.g., when the coil is not energized). The sealing mechanism 74 does not cover the third orifice 72 when the armature 40 moves toward pole piece 32. A fifth orifice 78 establishes fluid communication between the second chamber 56 and the oil pan 14 just above a level of fluid in the pan 14 represented by D.

The various chambers and orifices described above establish armature travel times indicative of various oil conditions such as oil viscosity and an oil change occurrence, as well as various oil levels in the pan 14, as described below. The sensor is also operable to determine oil temperature.

Oil Level

The entire sensor 10 is positioned to be immersed in oil in the oil pan 14. When oil within the oil pan 14 is at a predetermined full level A, indicated both in FIGS. 1 and 2, armature travel time is a function of the sum of the resistances to fluid travel through each of the orifices 36, 68, 64, 58, 78 and 72, with viscous drag on the armature and piston movement also having a slight effect. Because these resistances will vary as oil level varies, the oil condition system 18 can monitor and record oil level within the oil pan 14, recognizing the instant current oil level as being within one of four ranges: full oil level, overfill oil level, "quart low" oil level, and excessively low oil level. This information can be conveyed to a vehicle operator, if desired, by connecting a display monitor, such as on an instrument panel screen, to the controller 16 and programming the controller 16 to send a display signal to the monitor corresponding to the monitored oil level.

If oil level in the pan 14 is at any level below the fifth orifice 78, as indicated by "excessive low" oil level D in FIGS. 1 and 2, all oil is forced out of chambers 50, 42, and 56 on the first armature cycle. When the spring 52 biases the armature 40 and piston 46, air is drawn into chambers 50, 42, 56 instead of oil, since the orifices 36, 68, and 78 are above the oil level. On subsequent cycles, because only air is moving through the majority of the orifices, the armature movement time is relatively fast. Thus, the controller 16 will recognize such an armature travel time as indicative of an "excessive low" oil level, will store this information, and may be programmed to send to a display a notification to the vehicle operator of the need to add oil.

If oil level in the pan 14 is at any level below the second orifice 68, as indicated by the "quart low" oil level C in FIGS. 1 and 2, but above the fifth orifice 78, the armature chamber 42 will displace oil out of chambers 50, 42, and 56 on the first armature cycle. When the spring 52 biases the armature 40 and piston 46, air is drawn into chambers 50, 42, instead of oil because the orifices 36 and 68 are above the oil level. Because orifice 78 is now under the oil level, it will draw in oil when the sensor 10 is energized. On subsequent cycles, because only air is moving through the orifices 68 and 36, the armature movement time is slower than at the extreme low level. Thus, armature travel time will be a function of the sum of resistances to fluid flow through orifices 72, 58, 64, 68 and 36. Thus, the controller 16 will recognize such an armature travel time as indicative of a "quart low" oil level.

When oil is at any level above the second orifice 68, as indicated in FIGS. 1 and 2, and lower than the sixth orifice 36, the armature chamber 42, and the first and second body chambers 70, 56, will be constantly filled with oil as the armature 40 travels, and oil will be forced through orifices 72, 58, 64 and 68. The pole piece chamber 50 will be filled with air. This combination will create a unique armature travel time recognized by the controller 16 as indicative of a full oil level, and being a function of the sum of resistances to fluid flow through orifices 72, 58, 64, 78, 36, and 68.

If the oil level in the oil pan 14 is at any level above the sixth orifice 36, the pan is overfilled, as indicated by overfill level B in FIGS. 1 and 2. Forcing fluid through orifice 36 under pressure, as well as the additional viscous drag caused by oil in the pole piece chamber 50 will slow the armature 40 relative to armature travel time at a full oil level or any lower oil levels. Armature travel time will be a function of the sum of resistances to fluid flow through orifices 72, 58, 64, 78, 36, 68 and 36. The controller 16 will recognize such an armature travel time as indicative of an overfill condition.

Oil Viscosity

When the coil 30 is energized and deenergized, the armature 40 moves within the cavity 37, which includes the armature chamber 42. When the armature 40 moves away from the pole piece 32, pressure in the armature chamber 42 and pole piece chamber 50 is reduced and atmospheric pressure pushes fluid (whether oil or air) through second orifice 68 and sixth orifice 36, respectively, in the pole piece 32. Fluid is also drawn through the orifice 58, channel 57, channel 60, orifice 64 and channel 66 into the armature chamber 42 from the body chamber 56. Oil is also pushed through orifices 72 and 78 from chamber 56. When the armature 40 moves toward the pole piece 32, fluid (whether oil or air) within the armature chamber 42 is forced out of the second orifice 68 and the ball valve 62 selectively prevents fluid from exiting the armature chamber 42 through the orifice 58 as discussed above. Additionally, fluid in the pole piece chamber 50 is forced through the sixth orifice 36. Also, the pressure in the second body chamber 56 is reduced and atmospheric pressure forces fluid through the third orifice 72 and fifth orifice 78. By summing the total resistance to fluid flow of all of the various orifices and friction of the moving parts, this slows the armature movement such that by measuring the time of armature motion and then applying an algorithm, the response time corresponds to a value indicating the viscosity of the fluid.

The second orifice 68 is larger in size than the first orifice 58, or at least is configured along with channel 67 to create a greater hydraulic resistance than channel 57, orifice 58, orifice 64 and channel 66, creating a pressure differential in the armature chamber 42 and causing the sensor 10 to act as a pump. As discussed above, the ball valve 62 also contributes to the pumping action. Oil flowing through the orifices 58, 64 and 68, as well as channels 57, 60, 66 and 67 slows the armature 40. A higher oil viscosity causes the armature 40 to move more slowly as it is cycled, increasing the armature response time. Additionally, the volume of the second body chamber 56 increases as the armature 40 moves toward the pole piece 32, with oil drawn into the chamber 56 through orifices 72 and 78 and then pumped to the armature chamber 42 when the armature 40 moves away from the pole piece 32. The third orifice 72 is larger in diameter than the first orifice 58 and channel 57, causing a pressure differential as the armature 40 moves. The inductive "kick" that occurs at the end of the armature travel in the cycle is detected by the controller 16, which is connected to coil 30. The thicker the oil, the longer it will take for the inductive kick to occur. The total armature response time is then checked in a look-up table stored in the controller 16 to obtain the relative viscosity of the oil. Oil viscosity can thus be measured using the sensor 10 (except when oil is at an extreme low level (i.e., below orifice 78, such as at level D)).

The resistance of the sensor 10 may also be measured and the engine controller voltage controlled to control the operating current to the sensor 10. This reduces any effects of current variability on the armature response time. Limiting the voltage below 12 volts can slow the armature 40 even further to modify the response time versus viscosity relationship and thereby increase the sensor sensitivity.

Oil Change Occurrence

The oil condition and level sensor 10 is configured such that monitoring the current kick of the sensor 10 over numerous solenoid cycles can indicate an oil change occurrence. The elastomeric seal 74 traps any air within the first body chamber 70 when the sensor 10 is off (i.e., when the coil 30 is not energized). Alternative sealing structures, such as a check valve, metal seal, or needle valve, may also be used to trap air in the first body chamber 70. A conical feature 82 formed by the base portion 24 at the first body chamber 70 directs any air disposed in the first body chamber 70 to remain adjacent the third orifice 72 until pumped out of the first body chamber 70. During an oil change, oil is drained out of the pan 14, and oil also drains out of the first body chamber 70. Air will be trapped within the first body chamber 70 when the oil pan 14 is refilled with oil. The pressure differential due in part to the size difference of the orifices 58, 64, 78, and 72, with the movement of the armature and the size of the air bubble trapped in the first body chamber 70 thus dictates the number of operating cycles (armature reciprocation in the column 37 is a single cycle) before the air is pumped out of the first body chamber 70 and successive chambers 56 and 42. While the trapped air is being pumped through the sensor 10, response time varies, and then stabilizes when all of the trapped air has been expelled. Because air flows much more freely through the orifices and chambers, viscous drag of the oil will markedly slow the armature travel time when all of the air has been pumped out of the first body chamber 70, through the second body chamber 56, through the armature chamber 42, and back into the oil pan 14. The controller 16 is programmed to recognize this pattern of monitored armature travel times as indicative of an oil change occurrence.

Oil Temperature

The entire sensor 10 is positioned to be immersed in oil in the oil pan 14 when oil within the oil pan 14 is at a predetermined full level A, indicated both in FIGS. 1 and 2. As a result, the temperature of the coil 30 will reach the same temperature as the oil temperature. To measure oil temperature, the coil resistance is measured and then checked against a temperature look-up table stored within the controller to determine the temperature of the oil. Alternatively, the sensor 10 may be cycled with a predefined voltage. By measuring the current, the coil resistance can be calculated and then correlated with temperature.

Accordingly, the oil condition and level sensor 10, as part of the oil sensing system 18, is operable to determine oil level and oil change occurrence, as well as oil conditions such as oil temperature and oil viscosity. Other embodiments of oil condition and level sensors offer similar capabilities. For example, referring to FIG. 3, an oil condition and level sensor 110 has a solenoid body 120 that includes an outer portion 122, a unitary base and coil support 124, and an extension portion 128. The unitary base and coil support portion 124 surrounds a coil 130.

Figure 3:
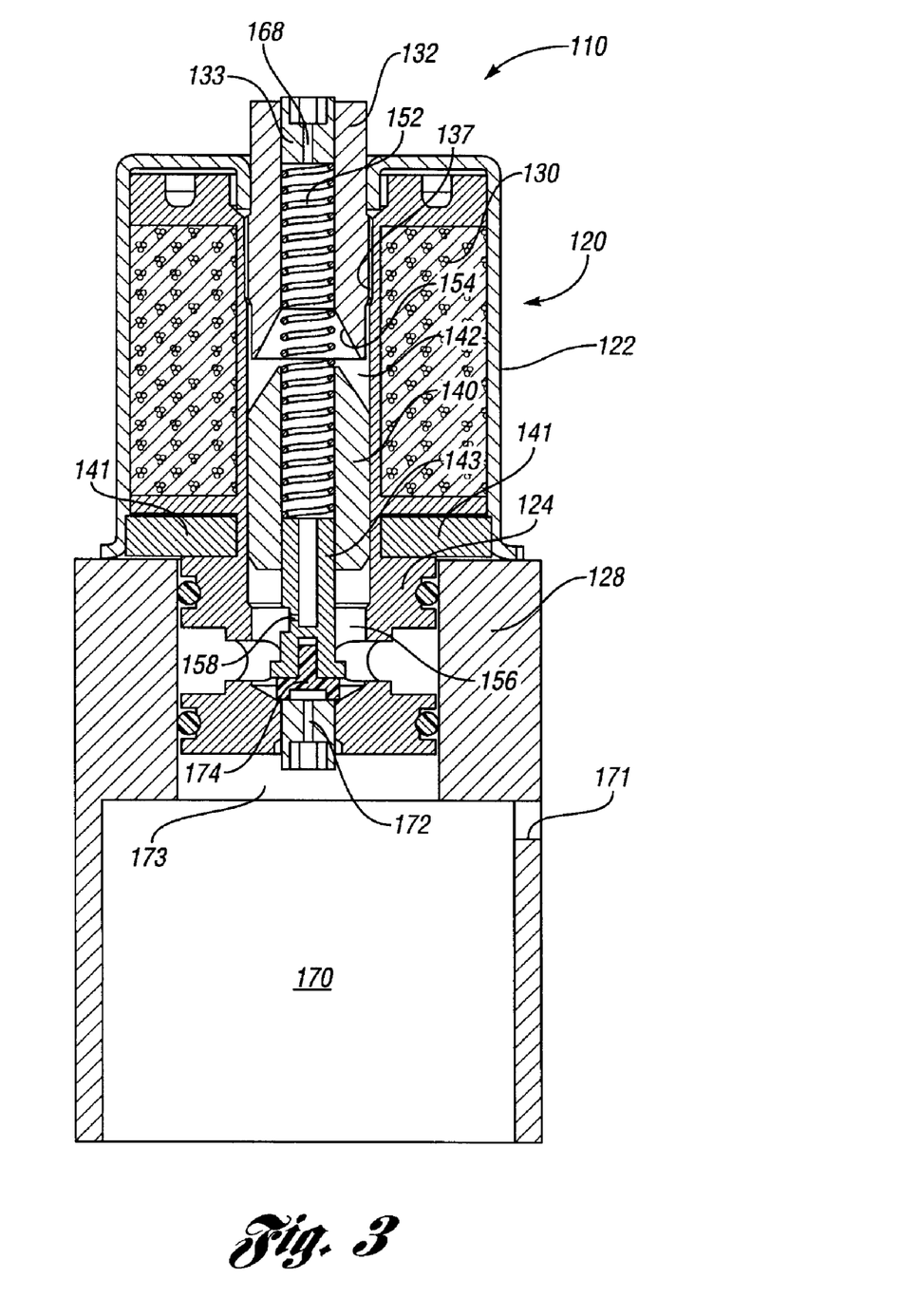
FIG. 3 is a schematic cross-sectional illustration of a second embodiment of an oil condition and level sensor.

Like the oil condition and level sensor 10, the oil condition and level sensor 110 can be positioned to be immersed in oil in the oil pan 14 when oil within the oil pan 14 is at the predetermined full level A, indicated both in FIGS. 1 and 2. As a result, the coil temperature will reach the same temperature as the oil temperature. To measure oil temperature, the coil resistance is measured and then checked against a temperature look-up table stored within the controller 16 to determine the temperature of the oil.

The oil condition and level sensor 110 includes a pole piece 132 press-fit or otherwise secured within the outer portion 122. A plug portion 133 of the pole piece 132 has an orifice 168 therethrough (the orifice 168 is referred to herein as a second orifice).

An armature 140 is movable within a columnar cavity 137 defined by the base and coil support portion 124, with the armature 140 partially defining an armature chamber 142 between the armature 140 and the pole piece 132 that varies in volume as the armature 140 moves in response to the flux created by energizing the coil 130. Flux collectors 141 are positioned adjacent the armature 140.

A biasing mechanism, which in this case is a spring 152, biases the armature 140 away from the pole piece 132. The pole piece 132 has an inner surface with a conical profile 154 interfacing with a like conical profile of an outer surface of the armature 140. The conical profile 154 distributes flux over a larger air gap adjacent the armature 140 than would a flat pole piece profile, thus slowing armature travel time.

A second body chamber 156 is formed in the base and coil portion 124. A first orifice 158 in an arm portion 143 of the armature 140 is in fluid communication with the second chamber 156. A third orifice 172 permits fluid communication between the second body chamber 156 and a first body chamber 170 formed in the extension portion 128. An orifice 171 permits fluid communication between the first body chamber 170 and the surrounding oil pan environment. Any air in the first body chamber 170 will rise and be held at the top portion 173 of the chamber 170, adjacent the orifice 172. An elastomeric seal 174 connected to the arm portion 143 of the armature 140 seals the third orifice 172 when the armature 140 is biased away from the pole piece 132. The first orifice 158 is smaller in diameter than the second orifice 168, which in turn is smaller in diameter than the third orifice 172. When the coil 130 is energized, the armature 140 displaces oil trapped in the armature chamber 142 out of both orifices 158, 168, and is also slowed by oil filling the second body chamber 156. Assuming oil level is such that the armature chamber 142 is filled with oil, the resistance to oil flow through orifices 158, 168 and viscous drag of the oil flowing through the chamber 142 provides resistance against the armature movement, slowing the stroke velocity of the armature and changing the signature (i.e., curve) of the solenoid current draw. A higher oil viscosity causes the armature 140 to move more slowly. The armature response time is checked in the lookup table stored in the controller 16 to obtain the relative viscosity of the oil.

The oil condition and level sensor 110 can be used to indicate a full oil level or a low oil level. A full oil level is indicated by the current draw when the oil level in the oil pan 14 is higher than the orifice 168, slowing discharge of the oil from the armature chamber 142. A low oil level is indicated by the current draw when the oil level in the pan 14 is lower than orifice 168, as air is drawn into the armature chamber 142 through orifice 168, allowing the armature 140 to move with less resistance. The oil condition and level sensor 110 can indicate an oil change occurrence by the pressure differential, due in part to the difference in orifice sizes of the orifices 172, 158, 168, movement of the armature 140, and the size of the air bubble trapped in the first body chamber 170. These factors dictate the number of armature cycles until all of the air is pumped out of the first body chamber and successive chambers 156 and 142 (i.e., until armature travel time slows and stabilizes in response to pumping oil in lieu of air) to indicate an oil change occurrence.

Figure 4:
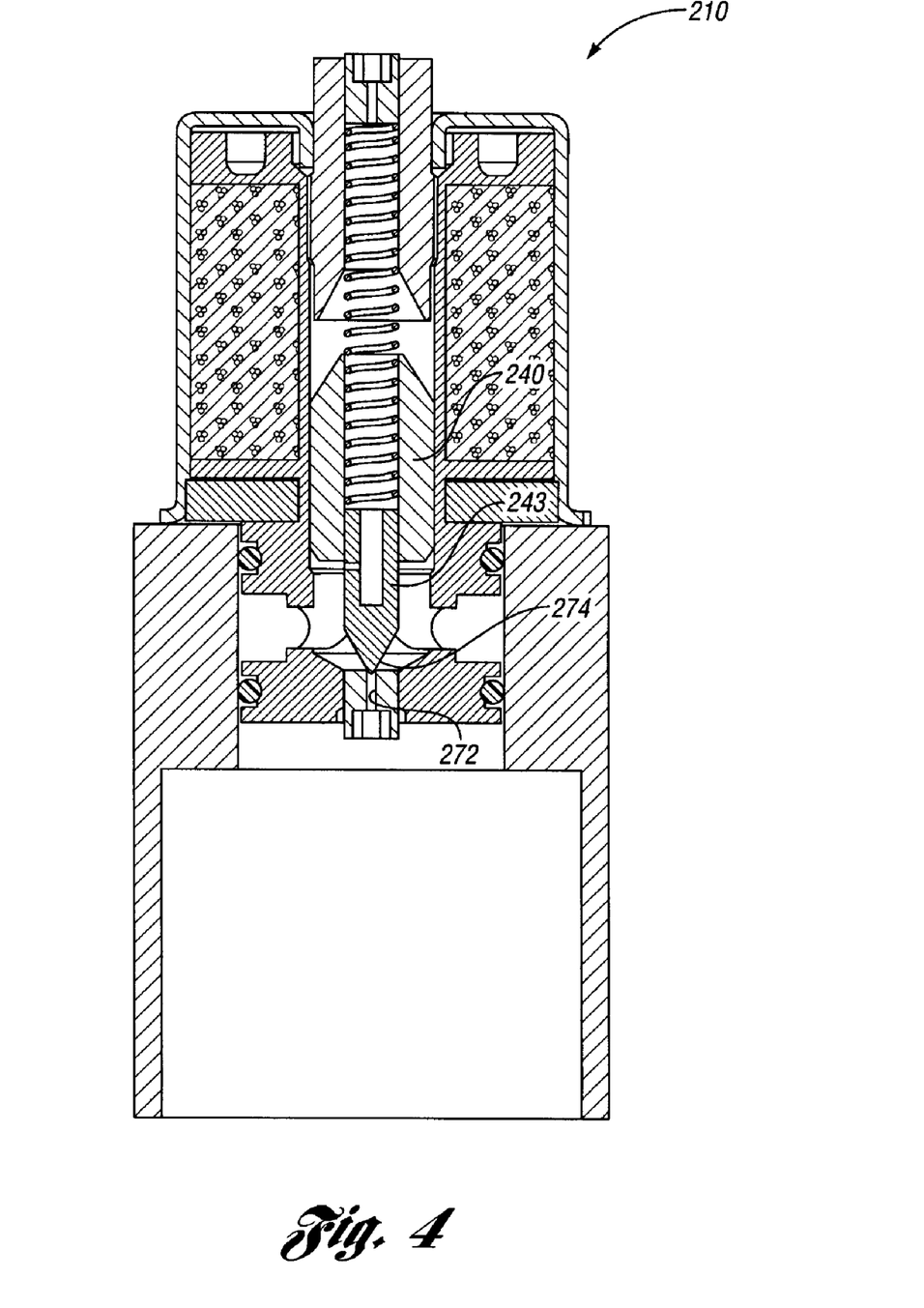
FIG. 4 is a schematic cross-sectional illustration of a third embodiment of an oil condition and level sensor.

Referring to FIG. 4, a solenoid sensor 210 is illustrated that is alike in all aspects and functions to solenoid sensor 110, except that the elastomeric seal 174 of sensor 110 is replaced by configuring the armature 240 with an arm portion 243 with a distal end having a conical shape 274. The conical shape 274 acts as a sealing mechanism by blocking the orifice 272, which serves the same function as orifice 172. Like components are referred to with the same reference numbers as with respect to the solenoid sensor 110.

Figure 5:
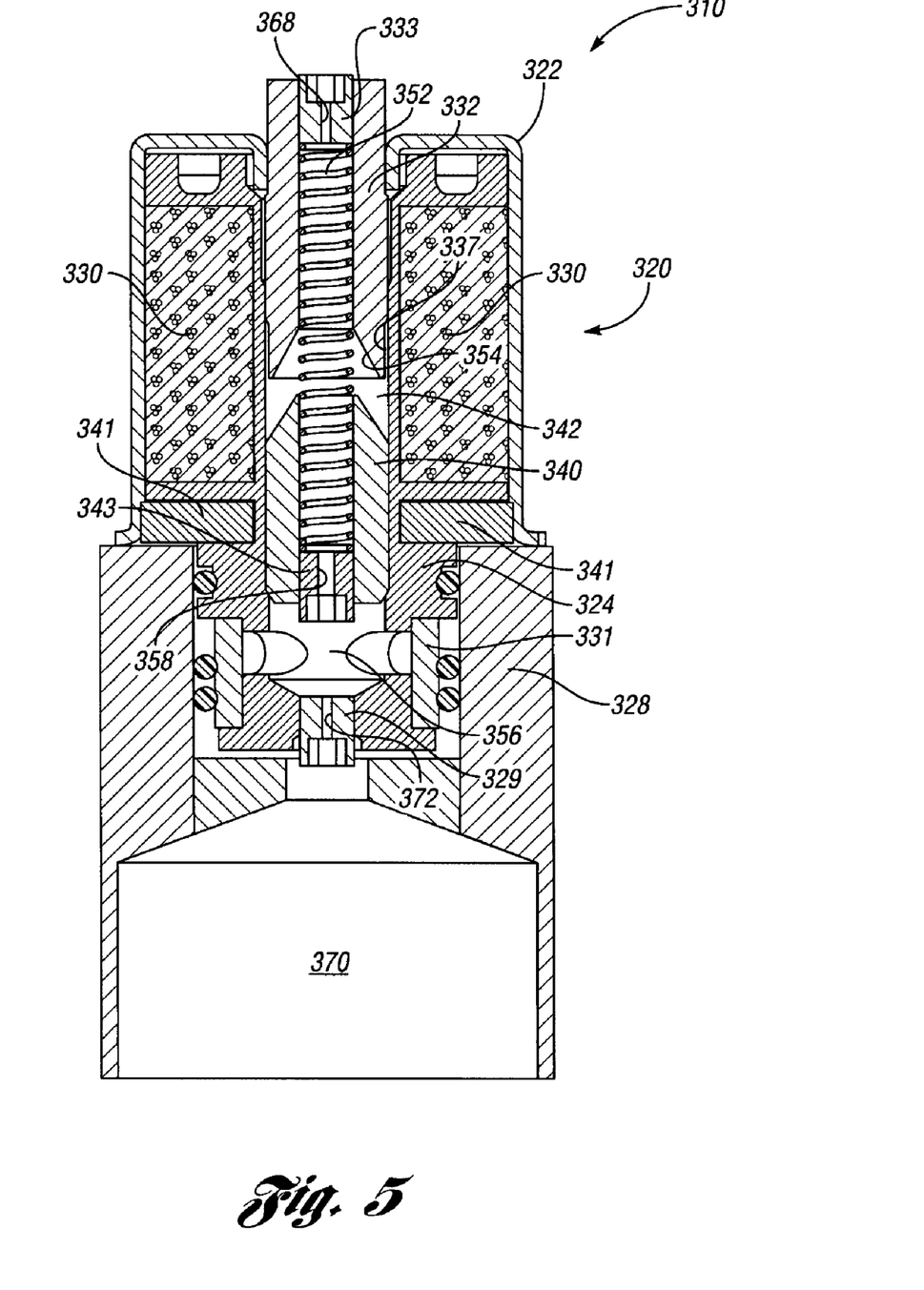
FIG. 5 is a schematic cross-sectional illustration of a fourth embodiment of an oil condition and level sensor.

Referring to FIG. 5, a solenoid sensor 310 is illustrated that functions like the solenoid sensor 110 of FIG. 3, except there is no sealing mechanism between the orifice 372 formed in a plug portion 329 of a solenoid body 320, which also includes an outer portion 322, a unitary coil support and base portion 324, an extension portion 328 and a chamber sealing portion 331.

The oil condition and level sensor 310 includes a pole piece 332 press-fit or otherwise secured within the outer portion 322. A plug portion 333 of the pole piece 332 has an orifice 368 therethrough (the orifice 368 is referred to herein as a second orifice).

An armature 340 is movable within a columnar cavity 337 defined by the base and coil support portion 324, with the armature 340 partially defining an armature chamber 342 (which is a portion of cavity 337) between the armature 340 and the pole piece 332 that varies in volume as the armature 340 moves in response to the flux created when coil 330 is energized. Flux collectors 341 are positioned adjacent the armature 340.

A biasing mechanism, which in this case is a spring 352, biases the armature 340 away from the pole piece 332. The pole piece 332 has an inner surface with a conical profile 354 interfacing with a like conical profile of an outer surface of the armature 340. The conical profile 354 distributes flux over a larger air gap adjacent the armature 340 than would a flat pole piece profile, thus slowing armature travel time.

A second body chamber 356 is formed in the base and coil portion 324. A first orifice 358 in a plug portion 343 of the armature 340 is in fluid communication with the second body chamber 356. A third orifice 372 permits fluid communication between the second body chamber 356 and a first body chamber 370 formed in the extension portion 328. Although no seal is disposed above the orifice 372 as in the sensor 110, the third orifice 372 is larger in diameter than the first orifice 358, creating a passive pumping action within the chamber 356 as the armature 340 reciprocates. Thus, the armature travel time is affected by not only the pumping of oil into an out of the chamber 340 through the orifices 358, 356, but also by the oil flow through orifice 372. The sensor 310 can be used to determine oil temperature, oil viscosity, an oil full level and an oil low level, in like manner as described with respect to the sensor 110.

A low content oil condition and level sensor, referred to as a two orifice design, not shown, may be configured like oil condition and level sensor 310, but without the body chamber 356, plug portion 329 and third orifice 372. Accordingly, the first orifice 358 would be in direct fluid communication with the lower body portion 370. Such an oil condition and level sensor would function like oil condition and level sensor 310, but would not slow armature travel time as much as with the third orifice 372, thus providing less gain of the current draw.

Oil Aeration and Oil Pump Function

In addition to the oil condition indications described above, the sensors 10, 110, 210 and 310 could be used to detect a level of aeration in the oil. Oil with greater aeration will be less viscous, will be easier to force through orifices, and will create less drag on the armature. This will result in faster armature travel times at a given oil level within the oil pan. The controller could be programmed to correlate such differences in armature travel time with oil aeration levels.

Additionally, the sensors 10, 110, 210 and 310 could be used on a vehicle to determine the volume of oil that is pumped into the engine at startup. Draw down of oil in the oil pan occurs when the engine pulls oil for lubrication and cooling at engine startup. The amount of draw down will create a difference in oil level in the oil pan, which may be detected by a difference in armature travel time as described above. Additional orifices and chambers may be added within the oil condition and level sensor to more closely track and distinguish various oil levels. Any discrepancy between the expected amount of draw down, stored as data within the controller, and the detected draw down, which the controller compares to the expected draw down, may indicate improper functioning of the engine oil pump.

While the best modes for carrying out the invention have been described in detail, those familiar with the art to which this invention relates will recognize various alternative designs and embodiments for practicing the invention within the scope of the appended claims.

The invention claimed is:

1. An oil condition and level sensor, comprising:
a solenoid body;
a coil, an armature, and a pole piece; wherein the solenoid body at least partially defines an armature chamber between the armature and pole piece; wherein the armature is movable in the armature chamber in response to energizing of the coil;
wherein the armature defines a first orifice in communication with the armature chamber; wherein the pole piece defines a second orifice in communication with the armature chamber; and wherein the orifices are configured such that fluid enters and is displaced from the armature chamber through the orifices as the armature moves, movement of the armature within the armature chamber thereby being affected by resistance to fluid flow through the orifices.

2. The oil condition and level sensor of claim 1, wherein the pole piece has a substantially conical profile configured to slow movement of the armature within the armature chamber.

3. The oil condition and level sensor of claim 1, wherein the pole piece defines a pole piece chamber; wherein the solenoid body defines another orifice in fluid communication with the pole piece chamber, and further comprising:
a piston within the pole piece chamber and movable in response to movement of the armature such that movement of the armature is affected by resistance to fluid flow through the another orifice when the piston moves in the pole piece chamber.

4. The oil condition and level sensor of claim 1, further comprising:
a biasing mechanism biasing the armature away from the pole piece.

5. The oil condition and level sensor of claim 1, wherein the first and second orifices are different sizes to create a pressure differential within the armature chamber.

6. The oil condition and level sensor of claim 5, wherein the first orifice is smaller than the second orifice.

7. The oil condition and level sensor of claim 1, wherein the solenoid body defines a first body chamber and a second body chamber; wherein the second body chamber is in fluid communication with the first orifice; and wherein the solenoid body defines a third orifice in fluid communication with both the first body chamber and the second body chamber.

8. The oil condition and level sensor of claim 7, wherein the solenoid body forms a conical feature at the first body chamber adjacent the third orifice.

9. The oil condition and level sensor of claim 7, further comprising:
a sealing mechanism between the armature and solenoid body configured to seal the third orifice.

10. The oil condition and level sensor of claim 9, wherein the sealing mechanism is an elastomeric seal.

11. The oil condition and level sensor of claim 9, wherein the sealing mechanism is a distal end of the armature.

12. The oil condition and level sensor of claim 9, further comprising:
a biasing mechanism configured to maintain the sealing mechanism at the third orifice when the coil is not energized; wherein the third orifice and the first and second body chambers are configured such that movement of the armature within the armature chamber is affected by resistance to fluid flow through the third orifice.

13. The oil condition and level sensor of claim 12, wherein the armature defines a channel in fluid communication with the first orifice and the armature chamber; and further comprising:
a check valve housed in the channel to selectively block flow from the armature chamber to the first orifice and the second body chamber when the armature moves in one direction, and to selectively permit flow from the second body chamber to the armature chamber through the first orifice and the channel when the armature moves in a direction opposite the one direction, the check valve thereby enabling positive displacement of fluid through the armature chamber.

14. An oil condition sensing system comprising:
a solenoid body;
a coil, an armature, and a pole piece; wherein the solenoid body defines an armature chamber between the armature and pole piece; wherein the armature travels in the armature chamber in response to energizing of the coil;
wherein the armature defines a first orifice in fluid communication with the armature chamber;
wherein the pole piece defines a second orifice in communication with the armature chamber; wherein the orifices are configured such that fluid enters and is displaced from the armature chamber through the orifices as the armature travels, travel time of the armature within the armature chamber thereby being affected by a sum of resistances to fluid flow through the orifices; and a controller operatively connected to the coil and operable to determine at least one of an oil temperature, oil viscosity, oil level, and oil change occurrence.

15. The oil condition sensing system of claim 14, wherein the pole piece has a substantially conical profile configured to slow movement of the armature.

16. The oil condition sensing system of claim 14, further comprising:

a check valve selectively blocking flow from the armature chamber to the first orifice when the armature moves in one direction and selectively permitting flow to the armature chamber through the first orifice when the armature moves in a direction opposite the one direction, thereby enabling positive displacement of the fluid through the armature chamber.

17. The oil condition sensing system of claim 14, wherein the solenoid body defines a first body chamber and a second body chamber; wherein the second body chamber is in fluid communication with the first orifice; wherein the solenoid body defines a third orifice in fluid communication with both the first body chamber and the second body chamber; and wherein the third orifice and the first and second body chambers are configured such that travel time of the armature within the armature chamber is further affected by resistance to fluid flow through the third orifice.

18. The oil condition and level sensor of claim 17, further comprising:

a sealing mechanism on the armature configured to seal the third orifice when the armature moves toward the third orifice; wherein air within the first body chamber is expelled from the sensor through the second body chamber and the armature chamber via the orifices as the armature moves, armature travel time thereby being affected by the expulsion of air and indicative of an oil change occurrence.

19. An oil condition and level sensor for an oil pan comprising:

a solenoid body;

a coil, an armature, and a pole piece; wherein the solenoid body defines an armature chamber between the armature and pole piece; wherein the armature travels in the armature chamber in response to energizing of the coil; wherein the armature, the pole piece and the solenoid body define multiple orifices and chambers; and wherein the orifices are configured to establish positive displacement of fluid through the chambers and orifices as the armature travels and to affect travel time of the armature in the armature chamber in correspondence with resistance to fluid flow through the orifices.

20. The oil condition and level sensor of claim 19 in combination with an oil pan configured to contain oil and a controller operatively connected to the coil; wherein the armature defines a first orifice in communication with the armature chamber;

wherein the pole piece defines a second orifice in communication with the armature chamber; wherein the solenoid body defines first and second body chambers and a third orifice; wherein the first and second body chambers are in communication with one another via a third orifice; wherein the second body chamber is in communication with the first orifice;

wherein the oil condition and level sensor is connected to the oil pan and positioned with the armature between the pole piece and the second body chamber, with the sensor configured to be at least partially immersed in oil at a predetermined full oil level, and with the first body chamber lower in the oil pan than the pole piece such that armature travel time is correlated by the controller with the predetermined full oil level when oil in the oil pan is above the second orifice, and with a second oil level lower than the predetermined full oil level when oil in the oil pan is below the second orifice but above the first orifice.

21. The oil condition and level sensor and oil pan of claim 20, wherein the armature defines a fourth orifice in fluid communication with the armature chamber, and a channel in fluid communication with the first and fourth orifices; wherein the solenoid body defines a fifth orifice in fluid communication with the second body chamber; and wherein armature travel time is correlated by the controller with a third oil level lower than the second oil level when oil in the oil pan is below the fifth orifice.

22. The oil condition and level sensor and oil pan of claim 21, wherein the pole piece defines a pole piece chamber; wherein the solenoid body defines a sixth orifice in fluid communication with the pole piece chamber, and further comprising:

a piston within the pole piece chamber and movable in response to movement of the armature such that movement of the armature is affected by resistance to fluid flow through the sixth orifice when the piston moves in the pole piece chamber; and wherein armature travel time is correlated by the controller with a fourth oil level higher than the predetermined full oil level when oil level is above the sixth orifice.

* * * * *